United States Patent
D'Aquila et al.

(10) Patent No.: US 10,881,344 B2
(45) Date of Patent: Jan. 5, 2021

(54) METHOD AND APPARATUS FOR ESTABLISHING AN INDIVIDUAL'S BEHAVIOR

(71) Applicant: GIPSTECH S.R.L., Rende (IT)

(72) Inventors: Gaetano D'Aquila, Rende (IT); Giuseppe Cutri', Rende (IT)

(73) Assignee: GIPSTECH S.R.L., Rende (IT)

( * ) Notice: Subject to any disclaimer, the term of this patent is extended or adjusted under 35 U.S.C. 154(b) by 600 days.

(21) Appl. No.: 15/532,952

(22) PCT Filed: Oct. 29, 2015

(86) PCT No.: PCT/IT2015/000260
§ 371 (c)(1),
(2) Date: Jun. 2, 2017

(87) PCT Pub. No.: WO2016/088145
PCT Pub. Date: Jun. 9, 2016

(65) Prior Publication Data
US 2017/0325731 A1    Nov. 16, 2017

(30) Foreign Application Priority Data

Dec. 2, 2014 (IT) .............................. CS2014A00034

(51) Int. Cl.
G01C 22/00   (2006.01)
H04W 4/029   (2018.01)
(Continued)

(52) U.S. Cl.
CPC .............. *A61B 5/16* (2013.01); *G01C 21/165* (2013.01); *G01C 21/206* (2013.01);
(Continued)

(58) Field of Classification Search
CPC ..... A61B 5/16; A61B 5/1116; A61B 5/02438; G01C 21/206; G01C 22/006;
(Continued)

(56) References Cited

U.S. PATENT DOCUMENTS

2010/0097269 A1    4/2010   Loidl
2011/0144457 A1*   6/2011   Coulon .................. A42B 3/046
                                                       600/301

(Continued)

FOREIGN PATENT DOCUMENTS

| EP | 2357450 A2 | 8/2011 |
| EP | 2357450 A3 | 10/2012 |
| WO | 2013/074352 A1 | 5/2013 |

OTHER PUBLICATIONS

Wikipedia: Dynamic time warping <https://web.archive.org/20141007115943/https://en.wikipedia.org/wiki/Dynamic_time_warping> retrieved by Archive.org on Oct. 7, 2014. (Year: 2014).*

(Continued)

*Primary Examiner* — Alexander Satanovsky
*Assistant Examiner* — Mark I Crohn
(74) *Attorney, Agent, or Firm* — Volpe Koenig

(57) ABSTRACT

A method and apparatus for reconstructing the behavior of an individual which provides:
  a detection operation, comprising recording monitoring signals using a detection apparatus carried by the subject;
  a mapping operation, comprising recording monitoring signals in an environment in which the behavior of the subject is to be reconstructed and the monitoring signals are to be associated with a map of the environment;
  an operation of reconstructing the behavior, comprising taking on as positions, over time, points on the map in which the monitoring signals recorded in the detection
(Continued)

operation correspond to the monitoring signals recorded in the mapping operation.

6 Claims, 2 Drawing Sheets

(51) Int. Cl.
    *A61B 5/024* (2006.01)
    *A61B 5/16* (2006.01)
    *G01C 21/16* (2006.01)
    *G01C 21/20* (2006.01)
    *H04L 29/08* (2006.01)
    *G01S 5/02* (2010.01)
    *A61B 5/11* (2006.01)

(52) U.S. Cl.
    CPC .............. *G01C 22/006* (2013.01); *G01S 5/02* (2013.01); *G01S 5/0205* (2013.01); *H04L 67/22* (2013.01); *H04W 4/029* (2018.02); *A61B 5/02438* (2013.01); *A61B 5/1116* (2013.01)

(58) Field of Classification Search
    CPC ......... G01C 21/165; H04L 67/22; G01S 5/02; G01S 5/0205; H04W 4/029
    See application file for complete search history.

(56) References Cited

U.S. PATENT DOCUMENTS

2014/0274122 A1* 9/2014 Tseng ...................... G01S 19/14
    455/456.1
2014/0368601 A1* 12/2014 deCharms ............. H04W 4/021
    348/14.02

OTHER PUBLICATIONS

Italian Patent Office Search Report and Written Opinion dated Jul. 17, 2015 (partially in English).
Notification of Transmittal of the International Search Report and the Written Opinion of the International Searching Authority for PCT/IT2015/000260 dated Mar. 2, 2016.

* cited by examiner

METHOD AND APPARATUS FOR ESTABLISHING AN INDIVIDUAL'S BEHAVIOR

FIELD OF THE INVENTION

The present invention relates to an apparatus and a method for reconstructing the behavior of an individual, in particular after an event.

In particular, the present invention relates to an apparatus and a method for reconstructing the behavior, and particularly the movements, of an individual, especially inside a building.

Therefore, the present invention is applicable in the field of security, and especially allows reconstructing the behavior of an operator during a security operation or more in general, of a security or rescue operator during activities which may be at risk.

BACKGROUND

In this field, micro cameras secured to the garments of an operator are used nowadays, which however often only allow a partial and limited reconstruction of the events filmed.

Instead, the need is strongly felt, particularly in the case of public safety operations followed by judicial proceedings, to reconstruct the behavior of the security operators and the methods in which such movements occurred in the most reliable manner possible.

The problem at the basis of the present invention is the one of allowing a reconstruction of the behavior of an individual after the event, in the most effective manner relative to the techniques used today.

It is the main task of the present invention to propose a method for reconstructing the behavior of the individual, particularly after the event, that has a solution to such a problem, thus resolving the drawbacks of the traditional techniques described above.

Within the scope of such a task, it is the aim of the present invention to propose an apparatus and a method for reconstructing the behavior of an individual, which allows reconstructing the movements of such an individual inside a building or generally, an indoor location, after the event.

SUMMARY

Another aim of the present invention consists in making an apparatus and a method for reconstructing the behavior of an individual, which allows correlating data relative to the vital parameters and/or to the posture of the latter with the movements of the individual.

Again an aim of the invention consists in proposing an apparatus and a method for reconstructing the behavior of an individual which can be implemented using widespread devices that are easy to transport.

This task, as well as these and other aims which will emerge more fully below, are attained by an apparatus and by a method for reconstructing the behavior of an individual according to the accompanying independent claims.

Detailed features of an apparatus and of a method for reconstructing the behavior of an individual according to the invention are indicated in the dependent claims.

BRIEF DESCRIPTION OF THE DRAWINGS

The following detailed description of the preferred embodiment of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

Figure 1:
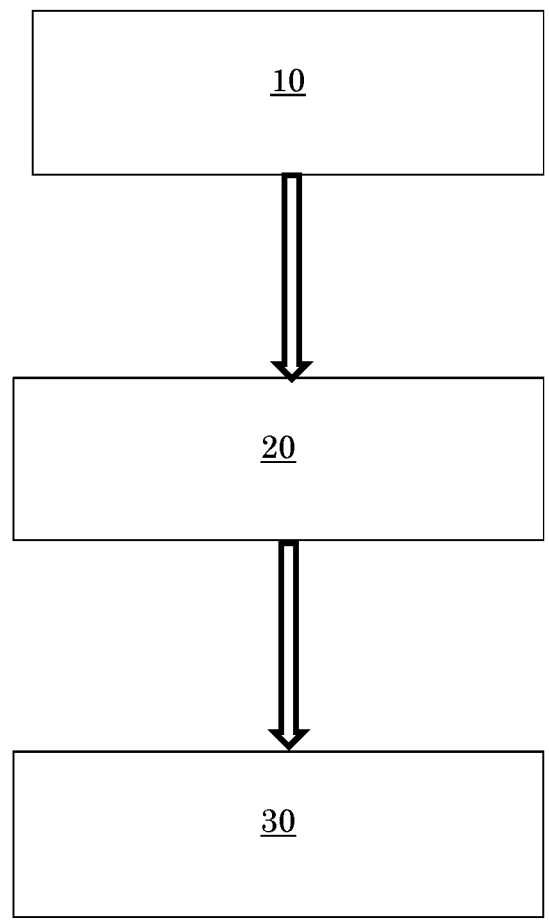
FIG. 1 is a flow diagram representing the method of the present invention.
Figure 2:
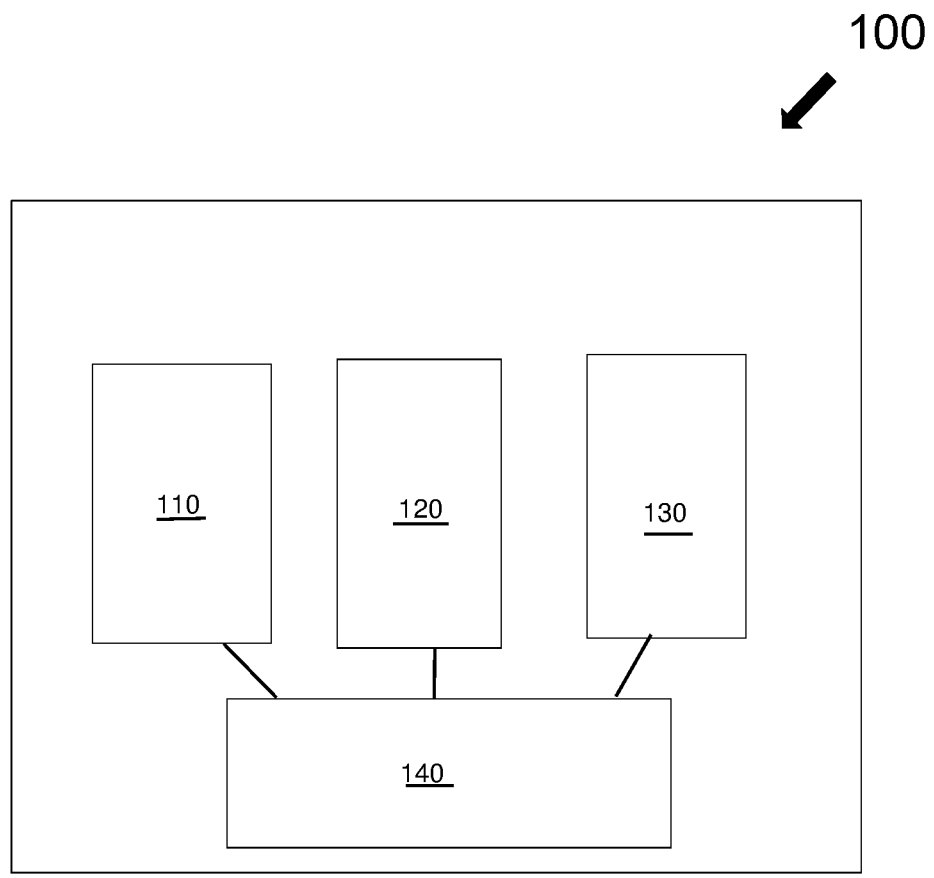
FIG. 2 is a schematic representation of the apparatus of the present invention.

Further features and advantages of the invention will emerge more fully from the description of a preferred but not exclusive embodiment of the method for reconstructing the behavior of an individual according to the invention, described by way of non-limiting example.

In accordance with the present invention, a method for reconstructing the behavior of an individual has a particular peculiarity in that it comprises:

DETAILED DESCRIPTION OF THE PREFERRED EMBODIMENTS

- a detection operation 10, which comprises recording monitoring signals using a detection apparatus 100 carried by the subject, preferably comprising environmental, natural and/or artificial, and inertial and biometric signals of the subject;
- a mapping operation 20, which provides recording monitoring signals in an environment in which the behavior of the subject is to be reconstructed and the monitoring signals are to be associated with a map of the environment;
- an operation of reconstructing the behavior 30, performed in separate time and following the detection operation, comprising taking on as positions of the subject, over time, the points on the map in which the monitoring signals recorded during the detection operation 10 correspond to the monitoring signals recorded during the mapping operation 20.

According to a peculiar aspect of the present invention, the operation of reconstructing the behavior is performed after, and in a moment of time separate from, the detection operation.

The operation of reconstructing the behavior is performed only following a specific request to reconstruct the behavior of the individual.

The mapping operation is also performed following, and in any event in a moment of time separate from, the detection operation and is performed only following a specific request to reconstruct the behavior of the individual.

The monitoring signals comprise at least environmental signals, such as for example geomagnetic signals and/or radio signals, and preferably also comprise inertial signals, detected for example using accelerometers and/or gyroscopes.

Performing the operation of reconstructing the behavior, and possibly also the mapping step, only following the detection operation allows performing the operation of reconstructing the behavior, and possibly the mapping operation, only if it proves to be essential, with great saving of resources.

Indeed, for example in the case of a public safety operation in which there may be a need to reconstruct the behavior of an agent, the operation of reconstructing the behavior, and especially the movement and the actions of the agent, is performed only if such a reconstruction is required and not systematically, as instead occurs in traditional localisation systems which comprise mapping as an essential prerequisite for localisation.

In particular, if it was not already performed beforehand for different reasons, the mapping operation is then also performed only if reconstructing the behavior of the individual proves to be essential.

As said, advantageously the monitoring signals comprise inertial signals and the operation of reconstructing the behavior comprises combining the inertial signals with the environmental signals detected so as to simultaneously define the localisation over time, that is the movements, the position, the dynamics and the posture of the individual.

Thereby, not only is it possible to reconstruct the position over time of the individual after the event due to the environmental signals, but it is possible to reconstruct the method of the movement, that is the position, the dynamics and the posture of the individual, due to the inertial signals.

It is indeed possible to reconstruct if over time the individual has run or walked, has bent down, has fallen, has jumped or has moved in a non-uniform manner, for example by zigzagging.

Preferably, to have an accurate reconstruction, the environmental signals can be obtained from gyroscopes and/or accelerometers and/or from luminosity sensors and/or from atmospheric pressure sensors and/or magnetic sensors and/or infrared sensors and/or noise sensors.

Advantageously, the detection operation comprises forming one or more time series representing the trend over time of the monitoring signals recorded during the detection operation.

Similarly, the mapping operation preferably comprises forming one or more time series of the trend over time of the monitoring signals recorded within the scope of the mapping operation, and associating the time series with trajectories on the map; where such trajectories are the ones which, when travelled, reveal the corresponding time series of the mapping operation have been detected.

The mapping operation preferably also includes the step of acquiring viability constraints of the space which are, for example inside a building, formed by constraints imposed by partition walls and other artificial objects such as tables, cupboards, etc.

Preferably, the operation of reconstructing the behavior similarly comprises a step of aligning the time series, performed so as to associate the time series recorded within the scope of the detection operation that can be aligned with the time series recorded within the scope of the mapping operation and corresponding to the trajectories, with trajectories of the map, so as to obtain the movements over time of the individual on the map.

Preferably the alignment step provides using a dynamic time warping algorithm, that is DTW, in order to obtain an effective and quick alignment.

The detection and mapping operation preferably comprise recording geomagnetic and/or radio signals in order to have an accurate and reliable localisation on the map.

In other words, according to a preferred aspect of the present invention, like the localisation operation, the detection operation comprises recording geomagnetic signals emitted by the environment where the individual is, using an apparatus carried or worn by the latter.

Such a device preferably records the geomagnetic signals detected during the movement of the individual, thus associating them with a time marker so as to form a time series.

The comparison after the event of such a time series with time series associated with a map of the environment, possibly created after the event, that is in a moment following the passage of the individual, allows reconstructing the trajectory, preferably rectilinear, of the individual on the map.

Preferably, such a comparison is performed using a DTW algorithm, as said above.

The expression "alignment" here is intended as a comparison operation between time series, aiming to determine the existing correspondence between them or to assess the similarity thereof.

In particular, such a comparison is implemented using a distortion operation of the sequences being compared, which is not linear with respect to the independent time variable.

Such an operation, which in itself is known and not further described, aims to find an optimal correspondence between the two sequences being compared, whereby the maximum probability is determined.

To integrate the information on the behavior, and especially on the movement, of the individuals with information on the status of the latter, the method according to the present invention advantageously comprises a bio-monitoring step which comprises detecting and recording biometric parameters of the individual over time.

Thereby, in addition to allowing a reconstruction of the movements of an individual after the events, the present method allows associating also the biometric status of the latter with them.

Therefore, it is possible for example, to reconstruct the whole of events which may have led to the injury or to the killing of the individual engaged in a public safety operation.

In other words, an application of the method the object of the present invention comprises equipping an individual with a detection apparatus designed to detect and record monitoring signals, and preferably geomagnetic signals.

During the movement of the individual in an environment, for example within a building, the detection apparatus records the monitoring signals.

So that, if required, it is then possible to compare the time series of such monitoring signals with mapped time series.

The mapped time series may have been detected and associated with the map of the environment both before and after the individual passed through the environment at hand.

In other words, the detection apparatus acts as black box for the individual to be monitored.

Indeed, if there is a need to reconstruct events connected to the movements of the individual, for example in a building, it is sufficient to
- map the building, that is detect the monitoring signals, for example geomagnetic and/or radio, and to associate them with the detection positions on the map of the building and
- align the time sequences of the monitoring signals detected by the detection apparatus with the ones obtained in the aforesaid mapping to reconstruct the movements of the individual in the building after the event.

As already said, mapping can already have been performed beforehand, but it can also be performed after the event without this minimally affecting the reliability and exploitability of the present method.

The mapping advantageously comprises:
positioning a detector for monitoring signals;
recording the monitoring signals detected by the detector;
associating the monitoring signals detected with the position of the detector;

reiterating the positioning, recording and associating operations, so as to form a map of monitoring signals associated with respective positions.

Preferably, the mapping comprises moving the detector in a zone to be mapped and recording, for each position taken on by the detector, the monitoring signals detected in the positions crossed along the movement.

Particularly, the mapping comprises:

indicating the starting point of the detector;

starting the detection of the signals by transporting the detector while traveling a path along the trajectory within the space;

indicating the end point of the movement.

Thereby, it is possible, through the due expedients, for example by performing a movement at constant speed, to automatically associate the measurement of the monitoring signal detected with every point of the space comprised between the starting point and the end point of the movement.

Likewise, an object of the present invention is an apparatus 100 for detecting monitoring signals which has a particular peculiarity in that it comprises:

a timer 110;

at least one monitoring sensor 120 designed to detect monitoring, environmental and/or inertial signals and preferably designed to detect geomagnetic signals;

at least one biometric sensor 130 designed to detect biometric signals of a subject;

preferably a battery powered system;

a control device 140 connected to the timer 110 and to the sensors 120, 130, and configured to record the monitoring and biometric signals and to form time series of the signals.

The control device is configured so as to be secured to a garment or to the body of the individual.

Preferably, the control device is configured to align the time series of the monitoring signals with the time series associated with trajectories on a map, in order to associate the movements of an individual with trajectories on the map.

The biometric sensor advantageously comprises a heart rate monitor which can be applied to the individual to be monitored.

In a specific embodiment of the invention, in the detection operation, geomagnetic and/or radio signals are recorded using the detection apparatus transported by the individual to be monitored.

This detection apparatus is likewise preferably configured both for detecting and recording inertial signals, for example being provided with accelerometers, and for detecting biometric signals of the individual.

Thus, the detection apparatus collects the trend over time of the environmental signals, of the inertial signals and of the biometric signals.

If there is a need to reconstruct the behavior of the individual, the environmental signals recorded will be used to reconstruct the movements of the individual and will be integrated with the inertial signals to reconstruct also the position, the dynamics and the posture of the individual during the movements.

The combination with the biometric signals will allow reconstructing the vital status of the individual during the movements reconstructed.

The invention as it is conceived is susceptible to numerous modifications and variants, all falling within the scope of protection of the appended claims.

Further, all the details can be replaced by other technically-equivalent elements.

In practice, the materials used, as well as the contingent forms and dimensions, can be varied according to the contingent requirements and the state of the art.

Where the constructional characteristics and the technical characteristics mentioned in the following claims are followed by signs or reference numbers, the signs or reference numbers have been used only with the aim of increasing the intelligibility of the claims themselves and, consequently, they do not constitute in any way a limitation to the interpretation of each element identified, purely by way of example, by the signs or reference numerals.

The invention claimed is:

1. A method for forensically reconstructing the behavior of an individual, just prior to the death or an injury of the individual, the method comprising:

a detection operation, comprising recording monitoring signals using a detection apparatus carried by the individual; the monitoring signals comprising at least environmental signals wherein the monitoring signals comprise inertial signals;

a mapping operation, comprising recording monitoring signals in an environment in which the behavior of the individual is to be reconstructed and the monitoring signals are to be associated with a map of the environment, the monitoring signals comprising at least environmental signals;

an operation of reconstructing the behavior, comprising taking on as positions of the individual, over time, points on the map in which the environmental signals recorded in the detection operation correspond to environmental signals recorded in the mapping operation and also comprises combining the inertial signals with the environmental signals so as to define the position, the dynamics and the posture of the individual;

the operation of reconstructing the behavior being performed after—and in a moment in time separate from—the detection operation and only following a specific request to reconstruct the behavior of the individual; the mapping operation is performed after—and in a moment in time separate from—the detection operation and only following a specific request to reconstruct the behavior of the individual, wherein the behavior of the individual is reconstructed by combining the inertial signals with the environmental signals so as to define the position, the dynamics and the posture of the individual.

2. The method according to claim 1, wherein the detection operation comprises forming time series of the trend over time of the monitoring signals recorded in the detection operation;

the mapping operation comprises forming time series of the trend over time of the monitoring signals recorded in the mapping operation, and associating the time series with trajectories on the map;

the operation of reconstructing the behavior comprising a step of aligning the time series in order to associate the time series recorded in the detection operation that can be aligned with the time series recorded in the mapping operation and corresponding to the trajectories, with trajectories of the map, so as to obtain the movements over time of the individual on the map.

3. The method according to claim 2, wherein the alignment step provides using a dynamic time warping algorithm.

4. The method according to claim 1, wherein the environmental signals detected in the detection and mapping operations comprise geomagnetic signals.

5. The method according to claim 1, further comprising a biomonitoring step comprising detecting and recording biometric parameters of the individual over time.

6. The method according to claim 1, wherein the behavior of the individual reconstructed is to determine whether the individual: ran, walked, bent down, fallen, jumped, moved in a uniform manner or moved in a non uniform manner.

* * * * *